(12) United States Patent
Gingrich et al.

(10) Patent No.: US 7,753,932 B2
(45) Date of Patent: Jul. 13, 2010

(54) MEDICAL DEVICE AND RELATED METHODS OF PACKAGING

(75) Inventors: Jon Gingrich, Shrewsbury, MA (US); Malka S. Berndt, Lexington, MA (US); Satish Sharma, Randolph, MA (US); Christopher D. Endara, Miami, FL (US); Otto E. Anderhub, Miami, FL (US); Michael Magill, Northborough, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1375 days.

(21) Appl. No.: 10/808,427

(22) Filed: Mar. 25, 2004

(65) Prior Publication Data

US 2005/0216029 A1 Sep. 29, 2005

(51) Int. Cl.
*A61B 17/28* (2006.01)
(52) U.S. Cl. .................................. 606/205; 248/205.5
(58) Field of Classification Search .................. 606/205, 606/208, 170; 604/528, 562, 564, 585, 103; 206/364, 363, 438; 242/169, 160.3, 160.2, 242/167, 170
See application file for complete search history.

(56) References Cited

U.S. PATENT DOCUMENTS

| | | | | |
|---|---|---|---|---|
| 2,587,707 A | * | 3/1952 | Dever | 242/388 |
| 5,027,478 A | * | 7/1991 | Suhr | 24/16 R |
| 5,344,011 A | * | 9/1994 | DiBernardo et al. | 206/364 |
| 5,364,355 A | * | 11/1994 | Alden et al. | 604/103.09 |
| 5,702,080 A | * | 12/1997 | Whittier et al. | 248/205.5 |
| 5,707,392 A | | 1/1998 | Kortenbach | |
| 6,299,630 B1 | * | 10/2001 | Yamamoto | 606/205 |
| 2004/0195132 A1 | * | 10/2004 | Sheetz et al. | 206/438 |
| 2007/0244514 A1 | * | 10/2007 | Weizman et al. | 606/205 |

* cited by examiner

*Primary Examiner*—Anhtuan T Nguyen
*Assistant Examiner*—Tuan V Nguyen
(74) *Attorney, Agent, or Firm*—Finnegan Henderson Farabow Garrett & Dunner, L.L.P.

(57) ABSTRACT

Embodiments of the invention relate to a medical device having a proximal portion that can selectively receive other portions of the device. More specifically, embodiments of the invention relate to an endoscopic instrument with a handle portion configured to accommodate an elongate, flexible member and an end effector assembly of the endoscopic instrument for protection, coiling, looping, containment, packaging and for disposal. The device may have a variety of configurations.

56 Claims, 15 Drawing Sheets

MEDICAL DEVICE AND RELATED METHODS OF PACKAGING

FIELD OF THE INVENTION

Embodiments of the invention relate to a medical device having a proximal portion that can selectively receive other portions of the device. More specifically, embodiments of the invention relate to an endoscopic instrument with a handle portion configured to accommodate an elongate, flexible member and an end effector assembly of the endoscopic instrument for protection, coiling, looping, containment, packaging and for disposal. The device may have a variety of configurations.

BACKGROUND OF THE INVENTION

Various medical instruments may be used in connection with an endoscope for performing a number of operations at a site deep within a patient's body cavity. One such instrument, a biopsy forceps device, samples tissue from a body cavity with minimal intervention and discomfort to patients. Typically, a biopsy forceps device, like other endoscopic instruments, has a long flexible tubular member (a catheter) for insertion into a lumen of an endoscope. The tubular member is sufficiently long and flexible to follow a long, winding path of the body cavity. For example, the elongate member may be 240 cm long or longer. An end effector assembly, such as a biopsy forceps assembly, is attached at a distal end of the tubular member, and a handle is attached at a proximal end of the tubular member. The handle may have an elongate portion and spool portion disposed around the elongate portion configured to move longitudinally relative to the elongate portion. An elongate mechanism, such as pull wires, extends through the tubular member to connect the end effector assembly and a portion of the handle, such as the spool. The pull wires may also be connected to the portion of the handle, such as the spool, via a hypotube. Longitudinal movement of the spool relative to the elongate portion of the handle causes the elongate mechanism to move longitudinally in the tubular member, which in turn causes the actuation of the end effector assembly.

The long flexible tubular member and end effector assembly are packaged, contained, protected, and/or disposed of in a variety of ways. For example, the long flexible tubular member can be looped or coiled so that it is more compact, and then tied by wrapping the distal most portion (a few inches thereof) around the coils or loops. In another example, a cap may be placed on the end effector assembly both to protect the end effector assembly and prevent it from getting caught on an external object or surface.

One problem with these arrangements, however, is that unraveling the device can be cumbersome and time consuming, and many times the tubular member becomes twisted and intertwined. Another problem is that the user may forget to remove the cap from the end effector assembly. As a result, the end effector assembly with the cap is advanced into the working channel of the endoscope, and the protective cap may come off and become lodged in the endoscope, rendering the endoscope unusable. For at least these reasons, other devices and methods for packaging, containing, protecting, and disposing of long flexible tubular members and end effector assemblies are desired.

SUMMARY OF THE INVENTION

In accordance with the invention, an embodiment of the invention includes a medical device including a handle, an end effector assembly, and an elongate, flexible member connecting the handle to the end effector assembly. The handle defines at least one groove configured to accommodate at least one of a portion of the elongate member and a portion of the end effector assembly.

Another embodiment of the invention includes a medical device including a handle, an end effector assembly, and an elongate, flexible member connecting the handle to the end effector assembly. At least one of a portion of the elongate member and a portion of the end effector assembly is disposed in at least one groove defined by the handle.

A further embodiment of the invention includes a method of packaging a medical device including providing a medical device including a handle, an end effector assembly, and an elongate, flexible member connecting the handle to the end effector assembly. The handle defines at least one groove configured to accommodate at least one of a portion of the elongate member and a portion of the end effector assembly. The method further includes forming at least one loop of the elongate member, and placing at least one of the at least one loop of the elongate member and the portion of the end effector assembly in the at least one groove.

Various embodiments of the present invention may include a handle including an elongate portion and a spool portion disposed around the elongate portion. Furthermore, the spool portion may include a proximal portion and a distal portion connected by a central portion. Additionally, the handle may include a channel and/or notch configured to accommodate the end effector. Alternatively, the handle may include a throughhole.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

The foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate embodiments of the invention and together with the description, serve to explain the principles of the invention.

DESCRIPTION OF THE EMBODIMENTS

Reference will now be made in detail to the present exemplary embodiments of the invention illustrated in the accompanying drawings. Wherever possible, the same reference numbers will be used throughout the drawings to refer to the same or like parts.

Various embodiments of the invention relate to an endoscopic instrument having a proximal portion that can selectively receive other portions of the device, including the elongate member and end effector assembly. Embodiments of the invention also relate to related methods of packaging and/or storing an endoscopic instrument. In such methods, the elongate member may be coiled or looped, for example to minimize the volume of the packaged device, and stored with the assistance of the proximal receiving portion. The end effector assembly also may be packaged and/or stored with the assistance of the proximal receiving portion, for example, to preserve the integrity of the end effector assembly and/or to protect the user during handling of the medical device. The proximal receiving portion may be a portion of the medical device itself, such as a portion of the proximal handle. Alternatively, the receiving portion may be a separate part coupled to the medical device and used for packaging and/or storing the medical device and not otherwise used in the medical procedure.

Figure 1:
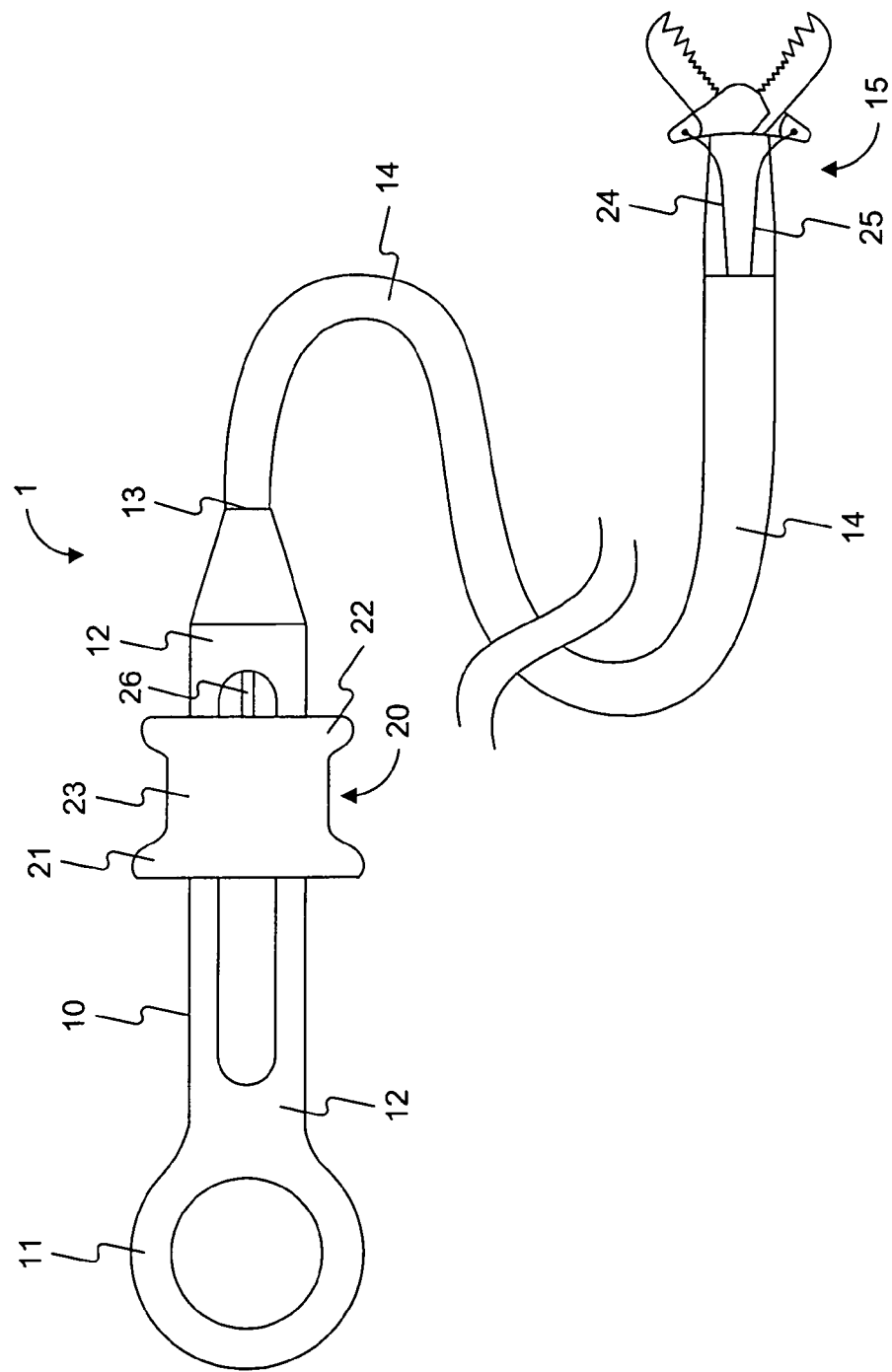
FIG. 1 is a plan view of an exemplary endoscopic instrument suitable for use in connection with embodiments according to the present invention.

An exemplary endoscopic instrument 1 which may be used in connection with a proximal receiving portion according to an embodiment of the invention is depicted in FIG. 1. The endoscopic instrument 1 has a handle 10, an elongate member 14, and an end effector assembly 15. The handle 10 includes a spool-like device 20 and a ring portion 11 attached to and/or integrally formed with an elongate portion 12. The device 20 is substantially coaxial with and disposed around the elongate portion 12, and is configured to move longitudinally with respect to the elongate portion 12. The handle 10, and more specifically the elongate portion 12, is connected to a proximal end of the member 14 via an elongate member interface 13. At its distal end, the member 14 is connected to the assembly 15, an example of which is shown in FIG. 1 as being a biopsy forceps device. The biopsy forceps device is only exemplary, however, and any other end effector assembly known in the art may be used as the assembly 15. Longitudinal movement of the device 20 relative to the elongate member 12 causes the actuation of the assembly 15. The device 20 causes actuation of the assembly 15 through control wires 24, 25 that are connected to the device 20 and the assembly 15, and extend through hollow portions of the elongate member 12 and member 14. The control wires 24, 25 are connected to the device 20 via a hypotube 26.

In various embodiments, the spool-like device 20 has proximal portion 21, a distal portion 22, and a central portion 23. During use, a user may insert a thumb into ring portion 11 and two fingers about central portion 23 to grip and actuate handle 10. In the embodiment shown in FIG. 1, the proximal portion 21 is larger in diameter than the distal portion 22, and both the proximal portion 21 and distal portion 22 have a larger diameter than the central portion 23. However, such a configuration is exemplary only, and any of the portions of the device 20 in FIG. 1, or in the various embodiments disclosed in this application, may have differing dimensions and sizes relative to each other.

The various embodiments of receiving portions of the medical device that selectively accommodate other portions of the medical device (such as member 14 and assembly 15) are described in connection with proximal handle 10. Specifically, the embodiments include the spool-like device including configurations that receive member 14 and/or assembly 15. Other portions of proximal handle 10, such as ring portion 11 and/or elongate portion 12 may be configured to have similar features as the spool-like device embodiments.

Figure 11A:
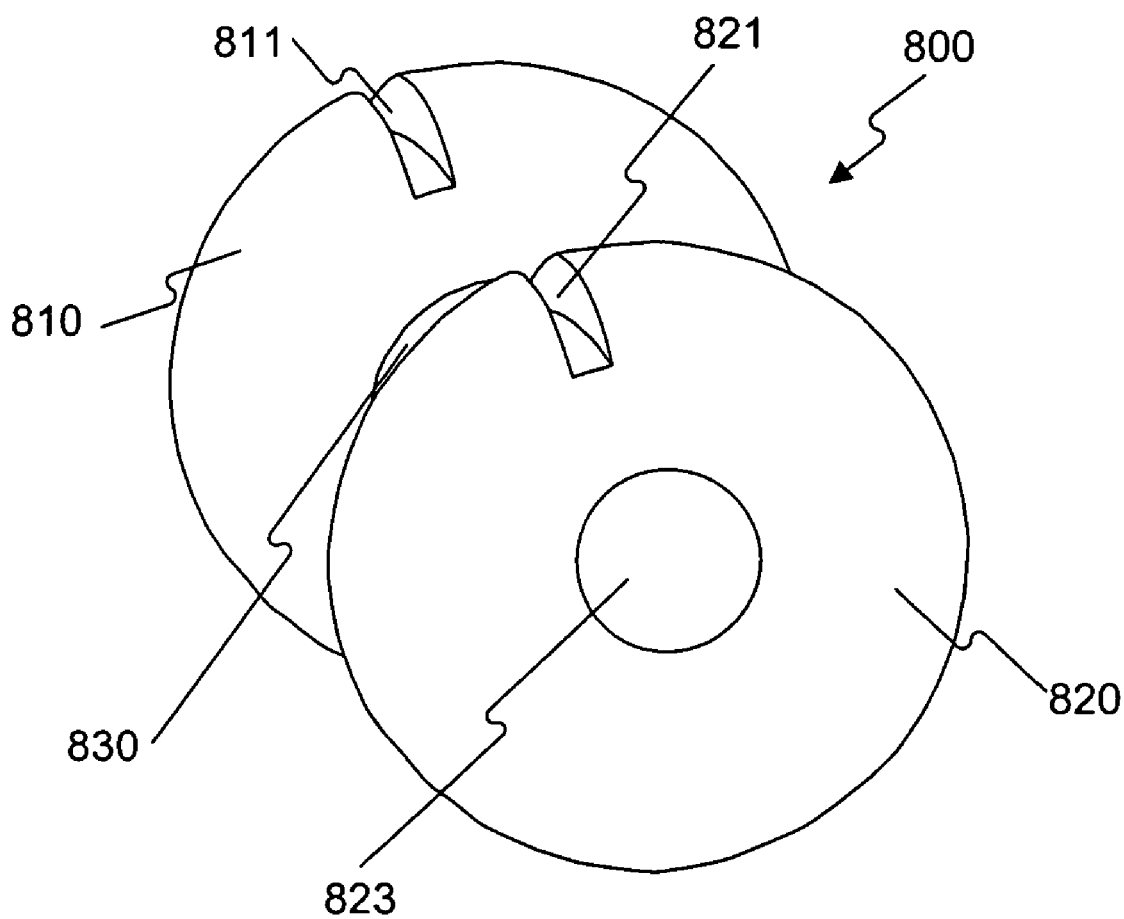
FIG. 11A is a perspective view of a portion of a proximal handle of an endoscopic instrument according to another embodiment of the present invention.
Figure 11B:
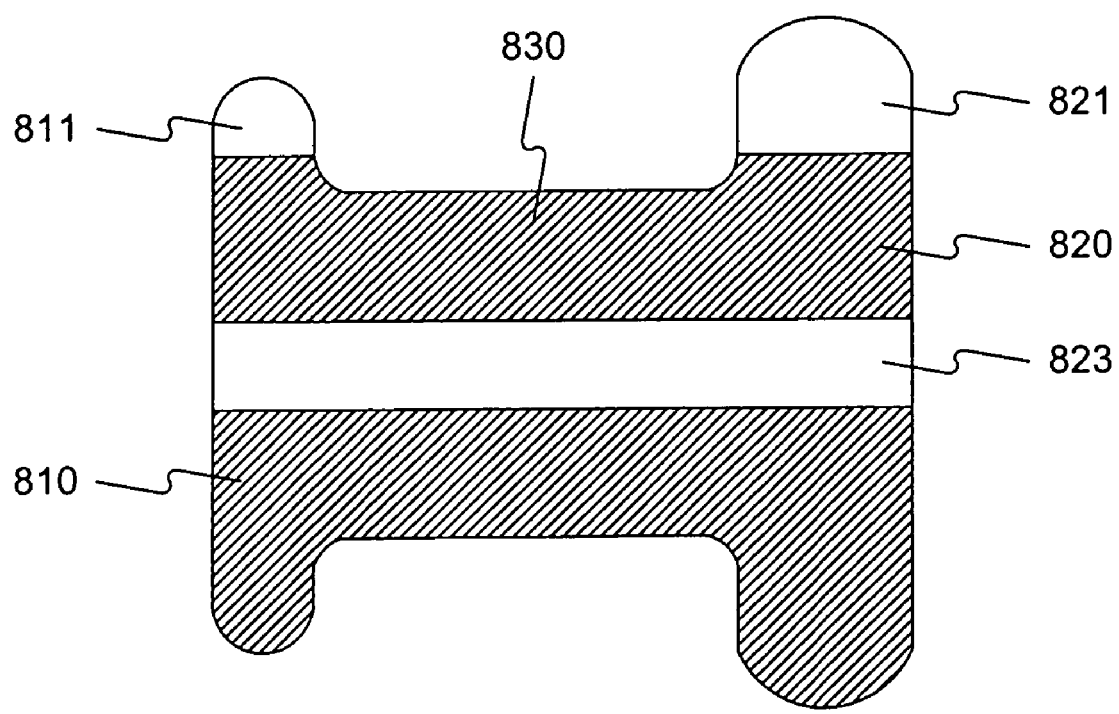
FIG. 11B is a cross-sectional view of the handle portion of FIG. 11A.

An embodiment of the spool-like device is depicted in FIGS. 11A-11B. The device 800 has a proximal portion 810, a distal portion 820, and a central portion 830. The proximal portion 810 has a groove 811 configured to accommodate at least one of a portion of the member 14 and at least a portion of the assembly 15. The distal portion 820 has a groove 821 configured to accommodate at least one of a portion of the member 14 and at least a portion of the assembly 15. The grooves 811, 821 may also be configured to accommodate more than one portion of the member 14, for example, multiple loops of the member 14 and/or at least a portion of the assembly 15. A throughhole 823 within device 800 (through portions 810, 820, and 830) is configured to accommodate the elongate portion 12 of the handle 10. At least one of the grooves 811, 821 may be composed of at least one material configured to allow the at least one groove to more effectively grip and/or retain at least a portion of the end effector assembly 15. The at least one material may comprise all or any portion of the spool 800, proximal portion 810, distal portion 820, and/or portions of the spool 800 that define the at least one groove 811, 821.

Figure 2:
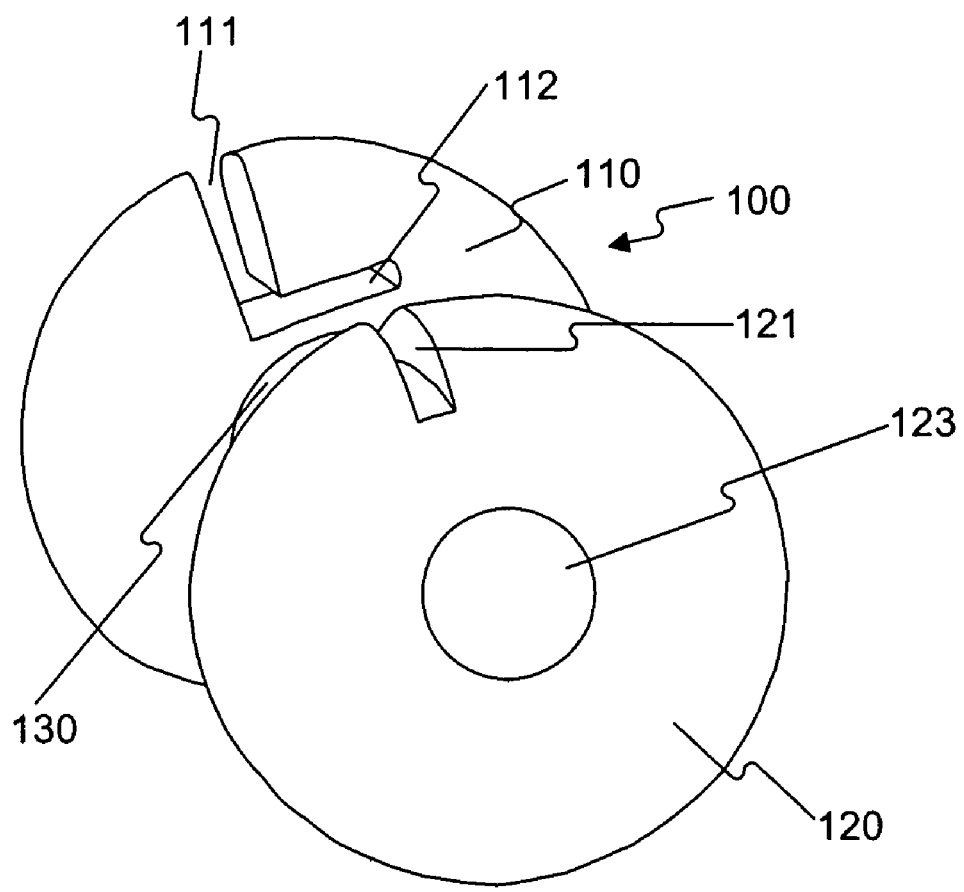
FIGS. 2-7 are perspective views of a portions of proximal handles of an endoscopic instrument according to different embodiments of the present invention.

A further embodiment of the spool-like device is depicted in FIG. 2. The device 100 has a proximal portion 110, a distal portion 120, and a central portion 130. The proximal portion 110 has a radial groove 111 and a circumferential groove 112 off the radial groove 111 configured to accommodate multiple loops of the member 14. A throughhole 123 within device 100 (through portions 110, 120, and 130) is configured to accommodate the elongate portion 12 of the handle 10. Various loops of the member 14 are placed through the radial groove 111 and then may be moved into the circumferential groove 112. Both the radial groove 111 and the circumferential groove 112 have a width greater than the diameter of the member 14, and have a combined length greater than the aggregate diameters of the desired number of loops of member 14 that will be placed there (e.g., at least three loops of the member 14). The circumferential groove 112 itself may have a sufficient length to accommodate all of the desired number of loops of member 14.

The distal portion 120 has a notch 121 configured to accommodate one loop of the member 14. The notch 121 has a width that is substantially the same as the diameter of the member 14, and a length sufficient to retain member 14, such as at least one-half the diameter of the member 14. Once the other loops of the member 14 have been placed in the radial groove 111 and circumferential groove 112 of the proximal portion 110, the last loop of the member 14 is placed in the notch 121 of the distal portion 120. The portion of the last loop of the member 14 placed in the notch 121 is near the distal end of the member 14 connected to the assembly 15. The notch 121 may be configured so that the member 14 does not fall out of the notch 121 despite minor jostling, for example, by having a width slightly narrower than the diameter of the member 14 so that the member 14 is press-fit into the notch 121.

Figure 9:
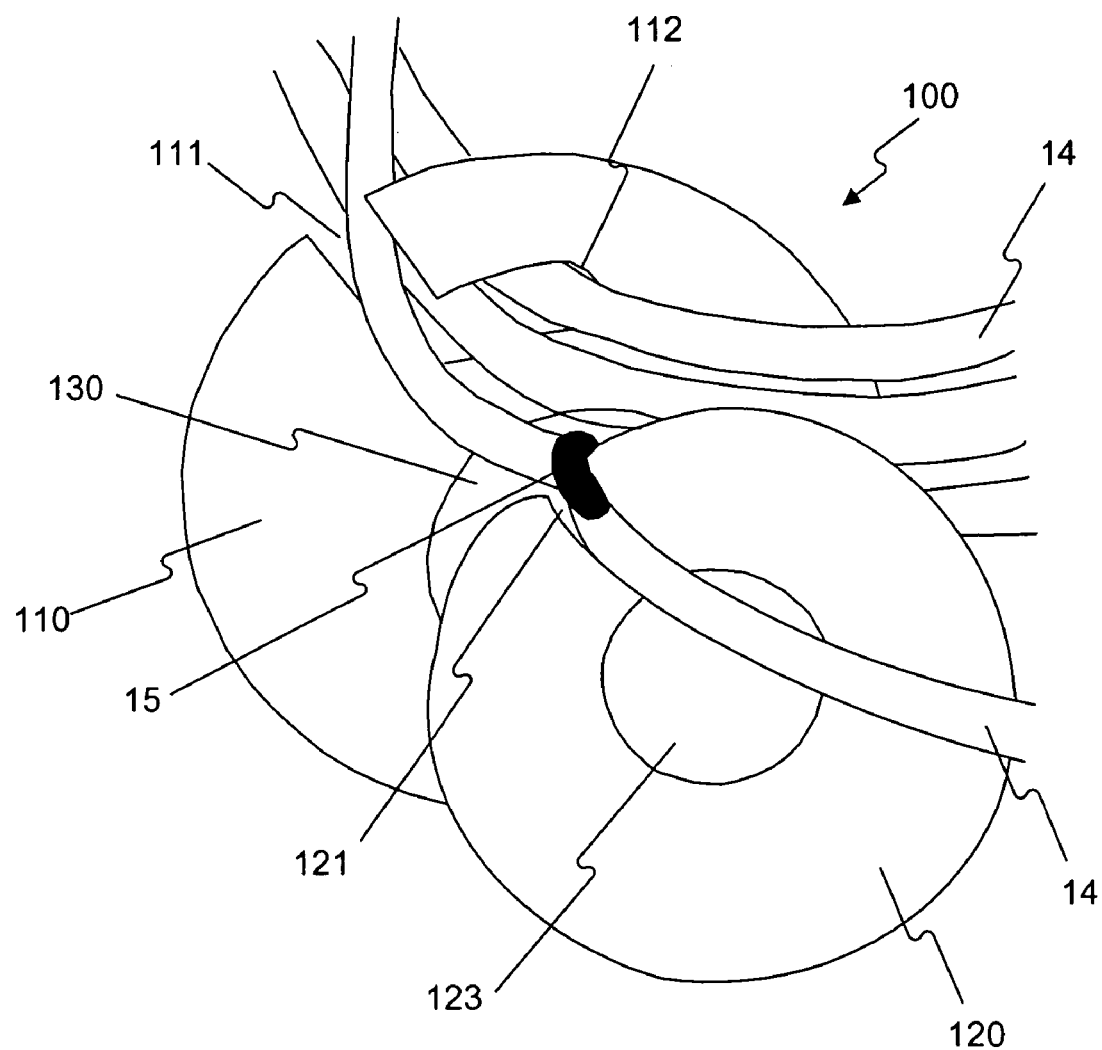
FIG. 9 is a perspective view of a portion of a proximal handle of an endoscopic instrument of FIG. 2, accommodating portions of an elongate member, according to an embodiment of the present invention.

FIG. 9 depicts an exemplary embodiment of loops of member 14 stored on the handle, for example, by being placed in grooves on the device. For example, FIG. 9 shows loops of member 14 stored in the device 100 of FIG. 2.

Figure 3:
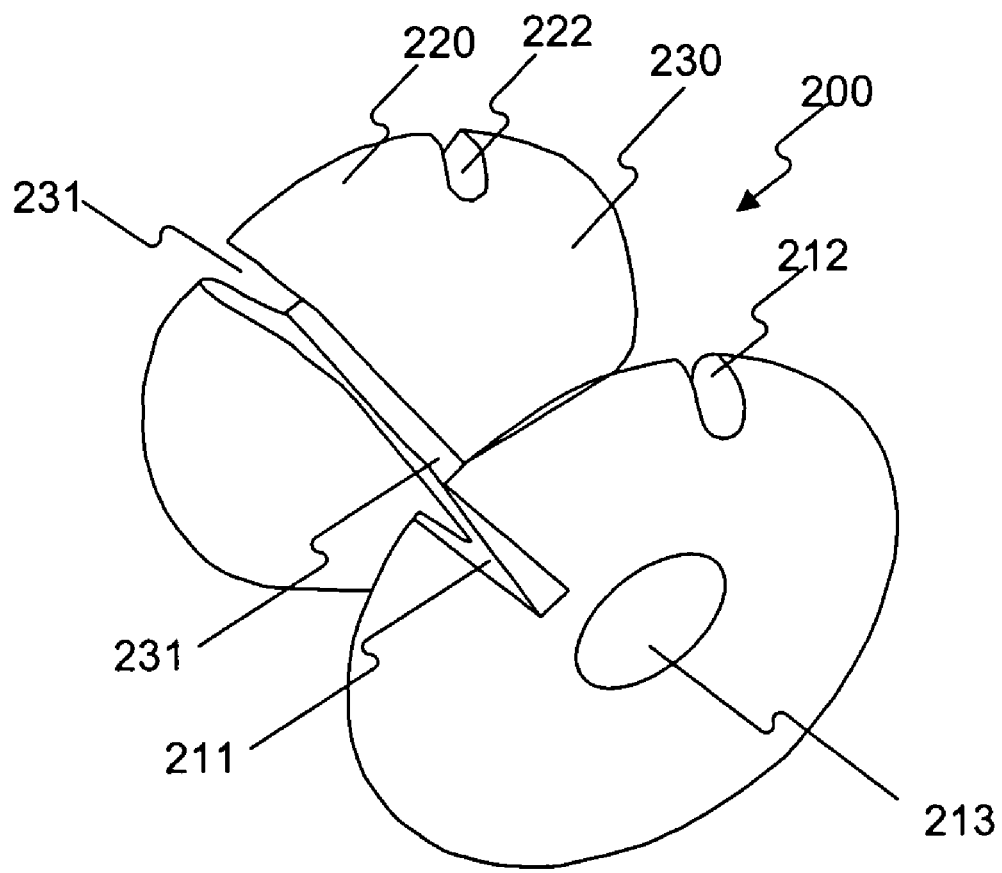

Another embodiment of a spool-like device is depicted in FIG. 3. The device 200 has a proximal portion 210, a distal portion 220, and a central portion 230. The proximal portion 210 has a groove 211 configured to accommodate multiple loops of the member 14, and a notch 212 configured to accommodate one loop of the member 14. A throughhole 213 within device 200 (through portions 210, 220, and 230) is configured to accommodate the elongate portion 12 of the handle 10. The groove 211 has a width greater than a diameter of the member 14 and a length greater than the aggregate diameters of the desired number of member 14 loops to be placed in the groove 211. The notch 212 has a width approximately the same as the diameter of the member 14, and a length sufficient to retain member 14, such as at least one-half the diameter of the member 14. The notch 212 may be configured so that the member 14 can be press-fit into the notch 212, for example, by having a width slightly narrower than the diameter of the member 14.

The distal portion 220 has a groove 221 substantially similar and corresponding to groove 211 on the proximal portion 210, and a notch 222 substantially similar and corresponding to groove 212 on the proximal portion 210. The desired number of loops of member 14 are placed in grooves 211, 221, and then the last loop is placed in notches 212, 222. The portion of the last loop in the notches 212, 222 is near the distal end of the member 14 connected to the assembly 15.

The central portion 230 may have a groove 231 that connects the bottom portions of grooves 211 and 221. The groove 231 may accommodate at least a portion of a member 14 (e.g., less than one width).

Figure 4:
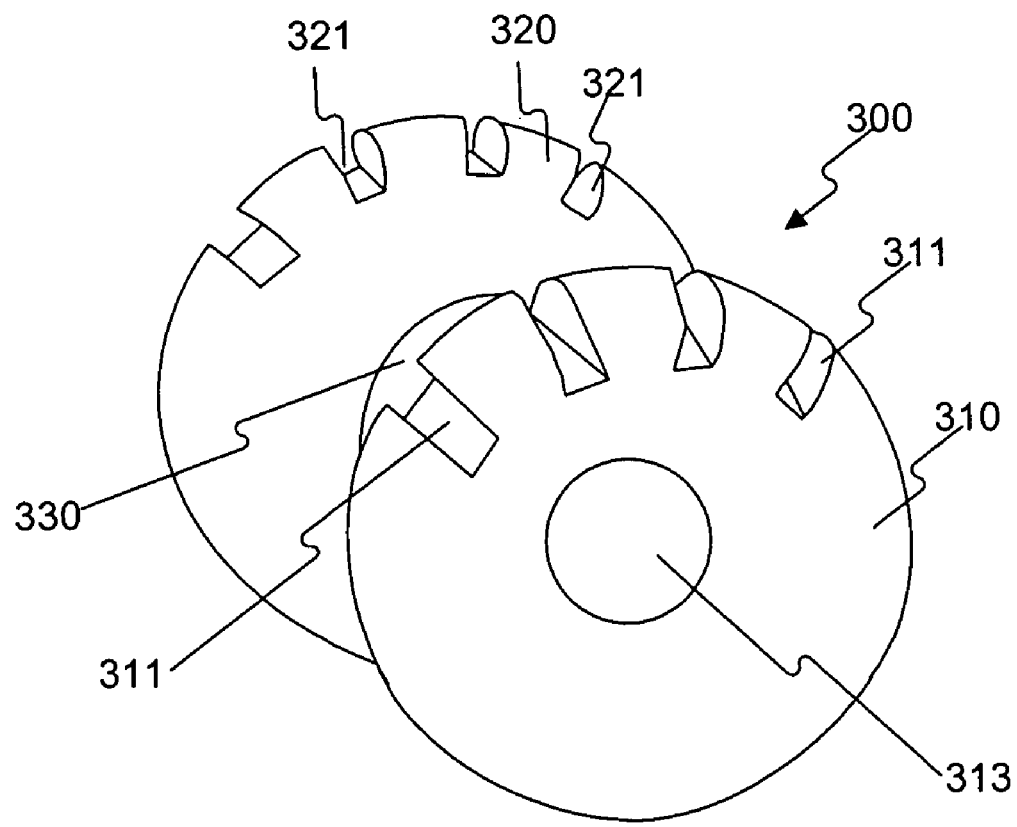

Another embodiment of a spool-like device is depicted in FIG. 4. The device 300 has a proximal portion 310, a distal portion 320, and a central portion 330. The proximal portion 310 has a plurality of grooves 311 each configured to accommodate at least one loop of the member 14. A throughhole 313 within device 300 (through portions 310, 320, and 330) is configured to accommodate the elongate portion 12 of the handle 10. Each groove 311 has a width dimension approximately the same as (i.e., slightly larger or slightly smaller than) the diameter of the member 14 and a length sufficient to retain member 14, such as at least one-half the width of the diameter of the member 14. Each groove 311 or a subset of the grooves 311 may be configured to allow the member 14 to be press-fit into the grooves 311. The distal portion 320 has a plurality of grooves 321 substantially similar and corresponding to grooves 311 on the proximal portion 310. One corresponding pair of grooves 311, 321 on the proximal portion 310 and distal portion 320, respectively, accommodates the last loop of the member 14 which is near the distal end of the member 14 connected to the assembly 15.

The loops of member 14 may be placed in the grooves 311, 321 in succession, for example the most proximal loop is placed in the first grooves 311, 321 and then each successive loop is placed in the next adjacent grooves 311, 321 going clockwise, so as to minimize tangling, and may be removed in the opposite order so as to minimize the same. However, in this or other embodiments, any of the loops of the member 14 may be placed in any of the grooves in any order. Furthermore, in this or other embodiments, there may be any number of grooves. For example, four grooves are shown in FIG. 4, however, the number of grooves in the various embodiments may vary, for example, based on the length of the medical device and/or the flexibility of the device (i.e., the ability of the device to form tight loops).

Figure 5:
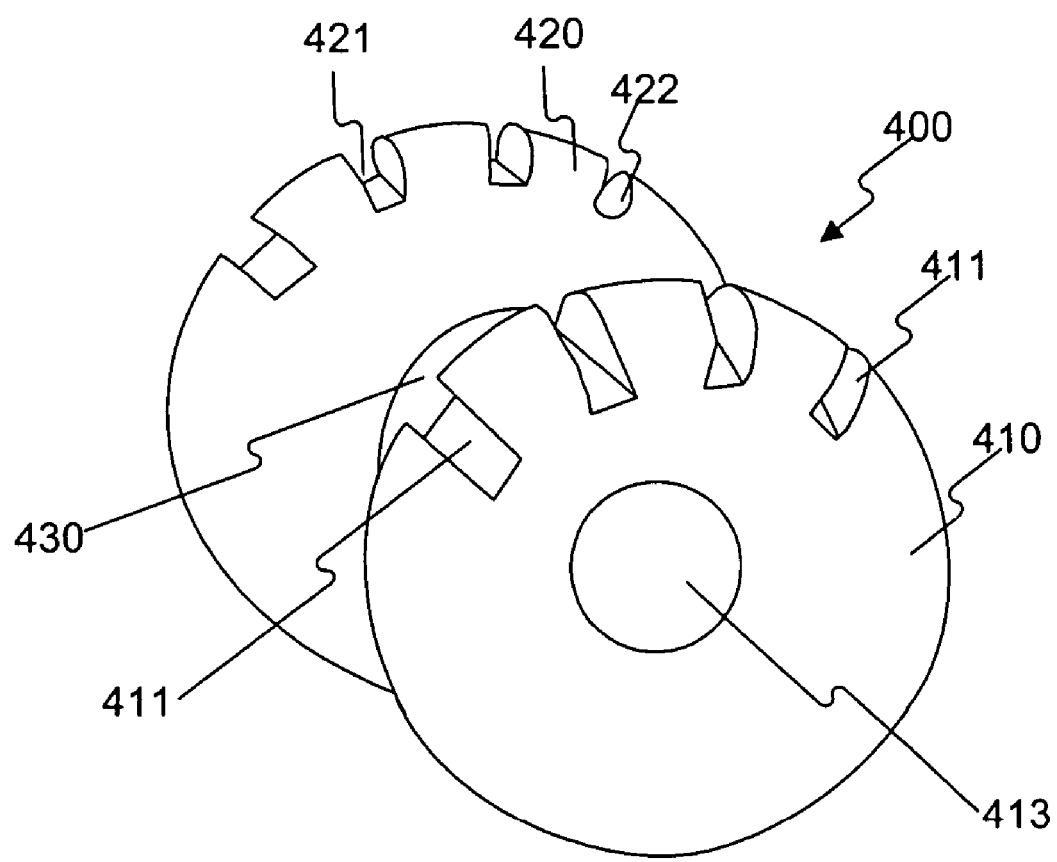

Another embodiment of a spool-like device is depicted in FIG. 5. The device 400 has a proximal portion 410, a distal portion 420, and a central portion 430. The proximal portion 410 has a plurality of grooves 411 configured to accommodate at least one loop of the member 14. A throughhole 413 within device 400 (through portions 410, 420, and 430) is configured to accommodate the elongate portion 12 of the handle 10. Each groove 411 has a width approximately the same as (i.e., slightly larger or slightly smaller) the diameter of the member 14 and a length sufficient to retain member 14, such as at least one-half the width of the diameter of the member 14. Each groove 411 or a subset of the grooves 411 may be configured to allow the member 14 to be press-fit into the grooves 411. The distal portion 420 has a plurality of grooves 421 substantially similar and corresponding to grooves 411 on the proximal portion 410. The distal portion 420 also has one notch 422, that corresponds to one of the grooves 411 of the proximal portion 410 and is configured to accommodate assembly 15 connected to the distal end of the member 14.

In this embodiment, the proximal loop of the member 14 is placed in the grooves 411, 421 furthest from the notch 422, and then each successive loop of the member 14 is placed in successive grooves 411, 421 going toward the notch 422, until the last loop of the member 14 is placed in groove 411 corresponding to the notch 422, and the assembly 15 is placed in the notch 422. The notch 422 is configured to hold at least a portion of the assembly 15 until removed by the user so as to both protect the assembly 15 from damage from outside elements, as well as to prevent the assembly 15 from interacting with the outside environment, including injury to the user. For example, if the assembly 15 is a biopsy forceps, the notch 422 would prevent the biopsy forceps from snagging or catching on anything else in the operating room environment, including the user or the patient. In such a case, the notch 422 could be shaped similarly to any portion of the assembly 15.

Figure 6:
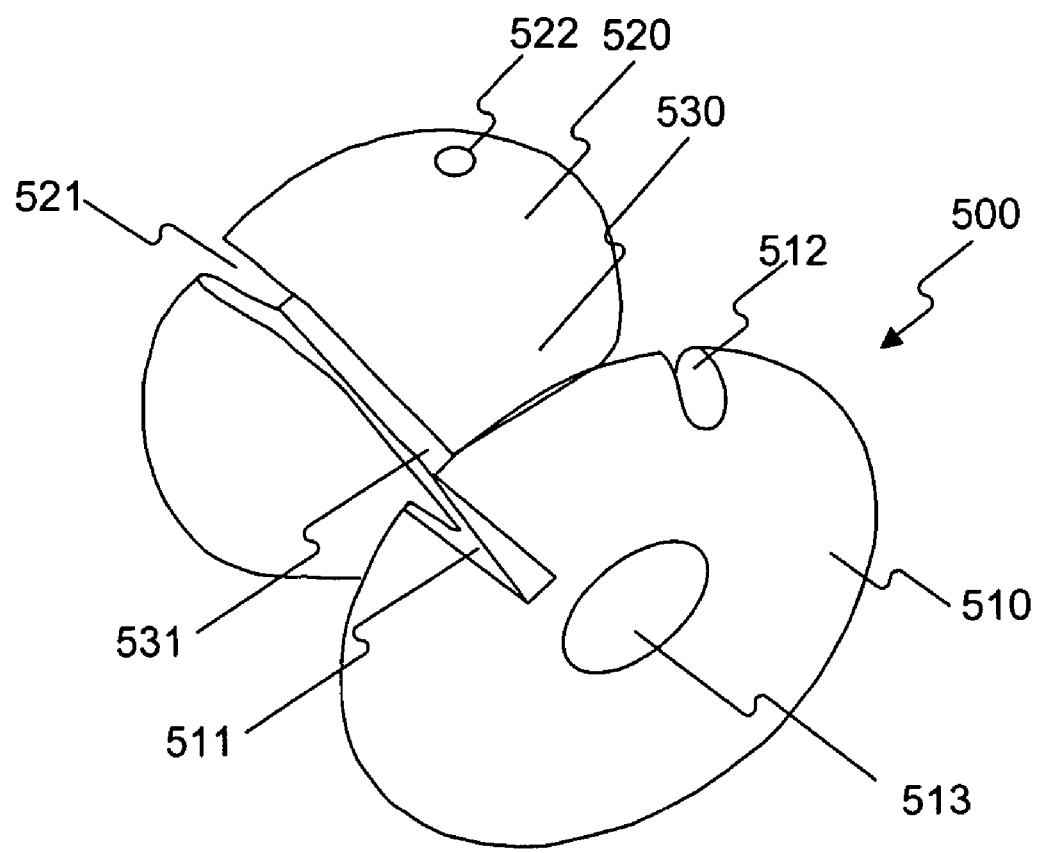

Another embodiment of a spool-like device is depicted in FIG. 6. The device 500 has a proximal portion 510, a distal portion 520, and a central portion 530. The proximal portion 510 has a groove 511 configured to accommodate multiple loops of the member 14, and a notch 512 configured to accommodate at least one loop of the member 14. A throughhole 513 within device 500 (through portions 510, 520, and 530) is configured to accommodate the elongate portion 12 of the handle 10. The groove 511 is substantially similar to the groove 211 in FIG. 3, and the notch 512 is substantially similar to the notch 212 in FIG. 3.

The distal portion 520 has a groove 521 configured to accommodate multiple loops of the member 14, and a channel 522 configured to accommodate at least a portion of an assembly 15. Channel 522 may have, for example, an internal surface that has a size and/or shape similar to an external surface of assembly 15. The groove 521 is substantially similar to the groove 221 in FIG. 3. The central portion 530 has a groove 531 substantially similar to the groove 231 in FIG. 3 The channel 522 on the distal portion 520 corresponds substantially to the circumferential location of the notch 512 on the proximal portion 510, and is set radially inward from the outer edge of the distal portion 520. Channel 522 extends partially through portion 520 or may extend through the entire width of the distal portion 520.

In this embodiment, the desired number of loops of the member 14 are placed in the grooves 511, 521, 531. The last loop of the member is placed in the notch 512, and then the assembly 15 is placed in the channel 522 for substantially the same reasons for placing the assembly 15 in the notch 422 of FIG. 5. The channel 522 may be adapted to be used with any assembly 15, and is also configured to prevent or at least discourage the assembly 15 from exiting the channel 522 without user interaction, for example, by slightly press fitting the assembly 15 into the channel 522.

Figure 10:
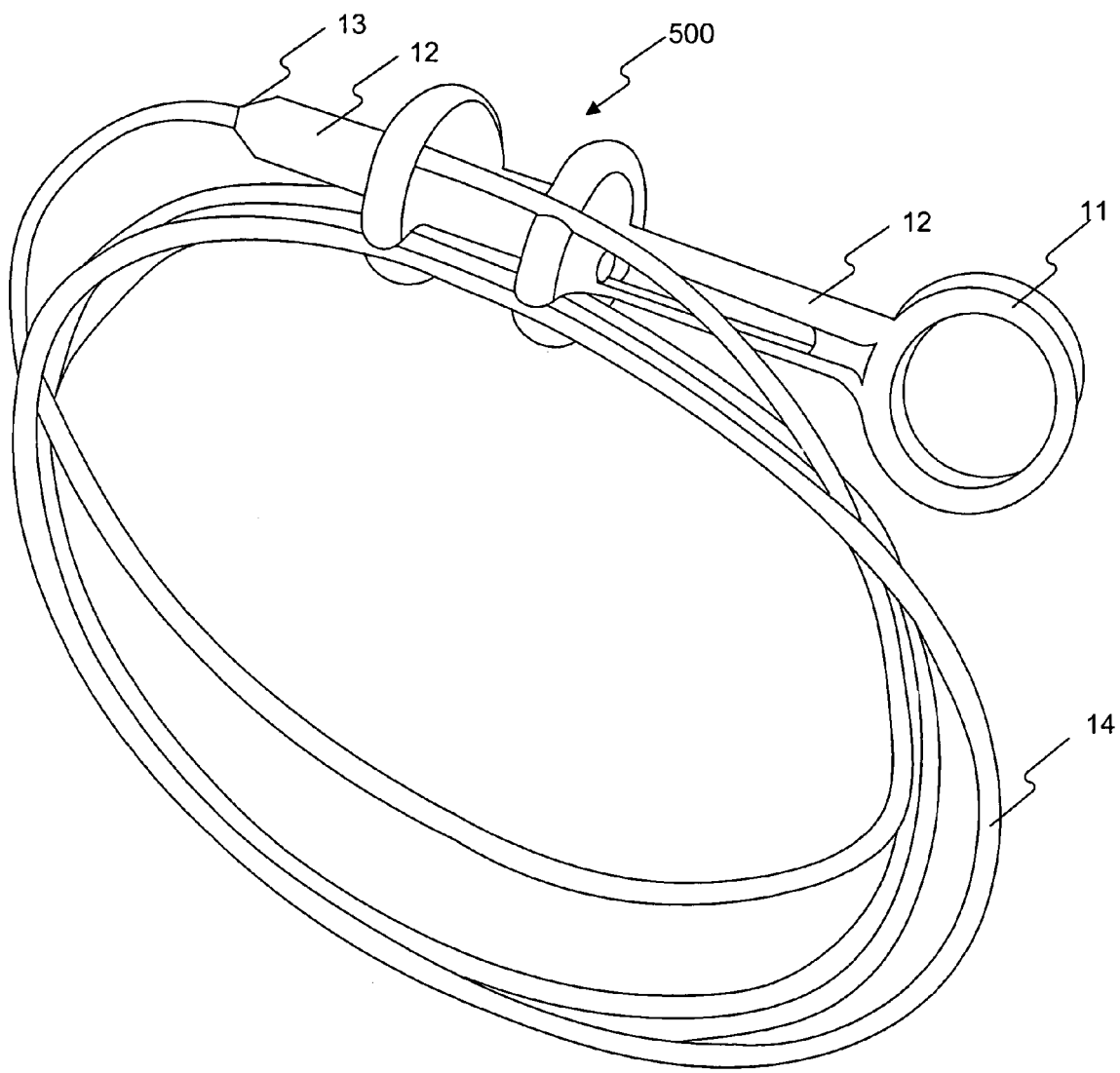
FIG. 10 is a perspective view of an endoscopic instrument of FIG. 6, accommodating portions of an elongate member, according to another embodiment of the present invention.

FIG. 10 depicts an exemplary embodiment of loops of member 14 stored on the handle, for example, by being placed in grooves on the device. For example, FIG. 10 shows loops of member 14 stored in the device 500 of FIG. 6.

Figure 7:
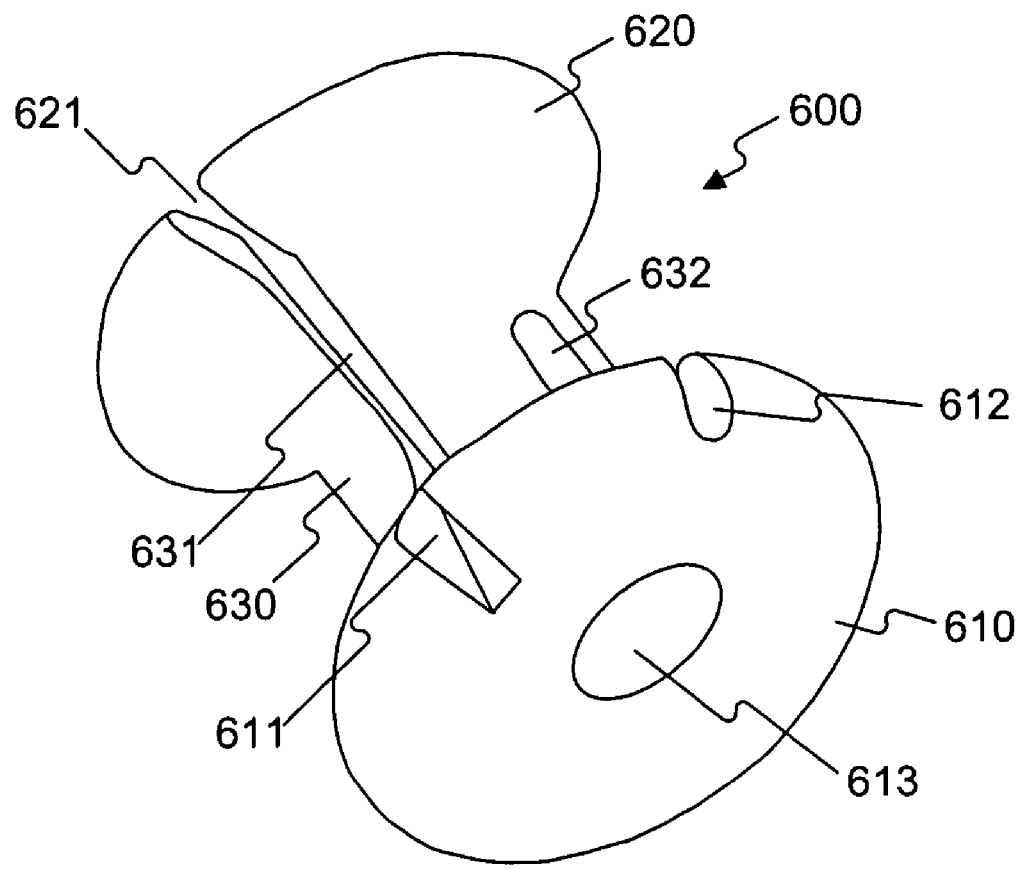

A further embodiment of a spool-like device is depicted in FIG. 7. The device 600 has a proximal portion 610, a distal portion 620, and a central portion 630. The proximal portion 610 has a groove 611 configured to accommodate multiple loops of the member 14 and a groove 612 configured to accommodate the assembly 15 and a portion of the member 14. A throughhole 613 within device 600 (through portions 610, 620, and 630) is configured to accommodate the elongate portion 12 of the handle 10. The groove 611 is substantially similar to the groove 211 in FIG. 3. The distal portion 620 has a groove 621 configured to accommodate multiple loops of the member 14. The groove 621 is substantially similar to the groove 221 in FIG. 3. The central portion 630 has a groove 631 configured to accommodate multiple loops of the member 14. The groove 631 is substantially similar to the groove 231 in FIG. 3. The groove 612 extends through substantially the entire width of the proximal portion 610 and may extend into a groove 632 on the central portion 630.

Figure 7A:
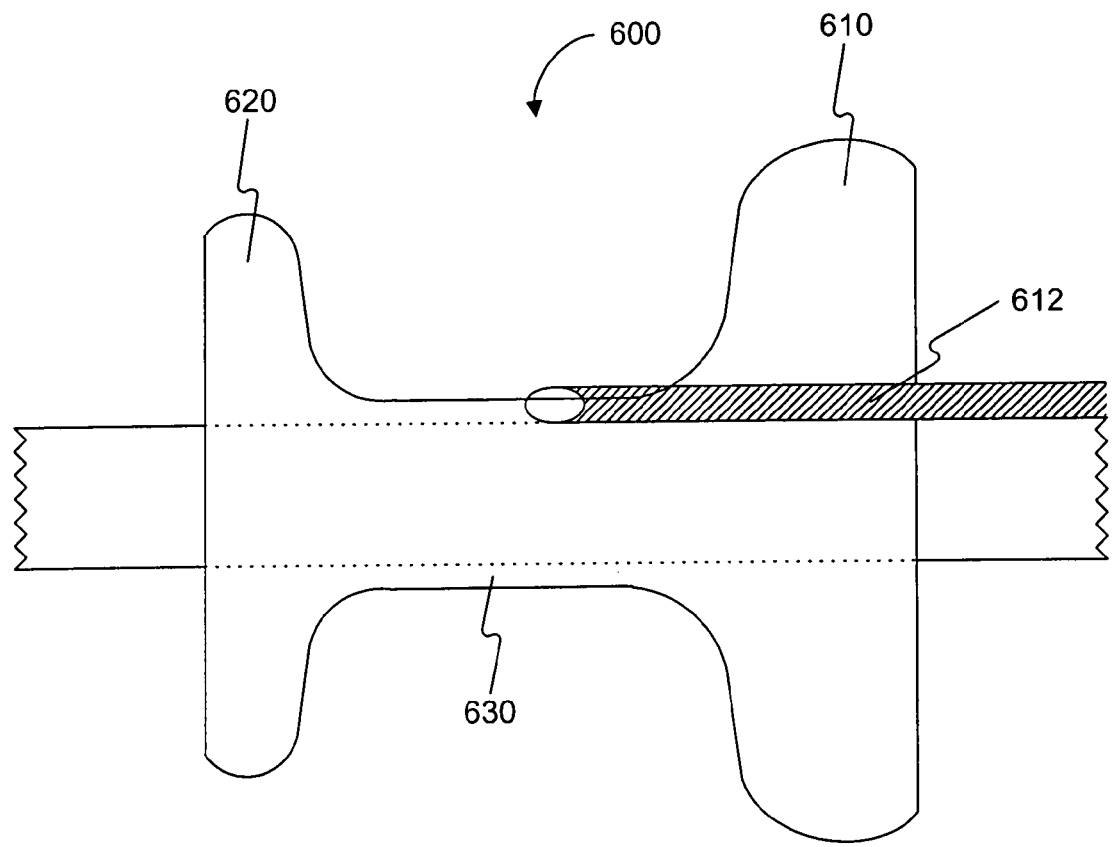
FIG. 7A is a schematic view of the proximal handle portion of FIG. 7, showing a spool portion accommodating an end effector assembly.

After placing the desired number of loops of member 14 into the grooves 611, 621, the assembly 15 on the distal end of the member 14 is placed into the groove 612 and advanced until either the assembly 15 is snuggly fitted into the groove 612, or the assembly 15 reaches the end of the groove 612, as shown in FIG. 7A. The assembly 15 may then continue to extend into groove 632 on the central portion 630. At this point, a portion of member 14 may or may not be in the groove 612 as well. As seen in FIG. 7A, a portion of the assembly 15 may emerge through the surface of the central portion 630, for example, so that the user can ascertain that the assembly 15 has been securely placed in the groove 612. The assembly 15 is placed in channel 612 for the same reasons the assembly 15 is placed in the notch 422 of FIG. 5.

Figure 8A:
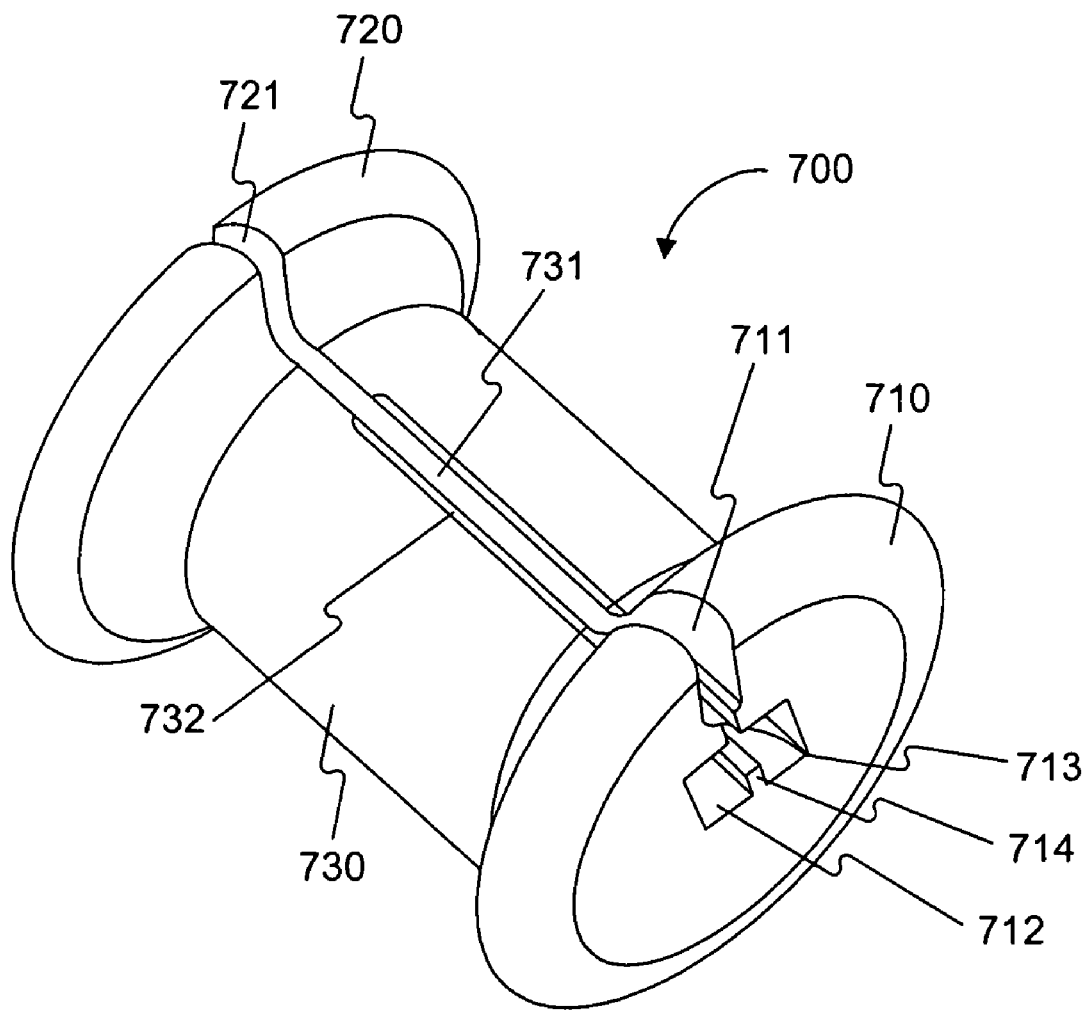
FIG. 8A is a perspective view of a portion of a proximal handle according to a yet further embodiment of the present invention.
Figure 8B:
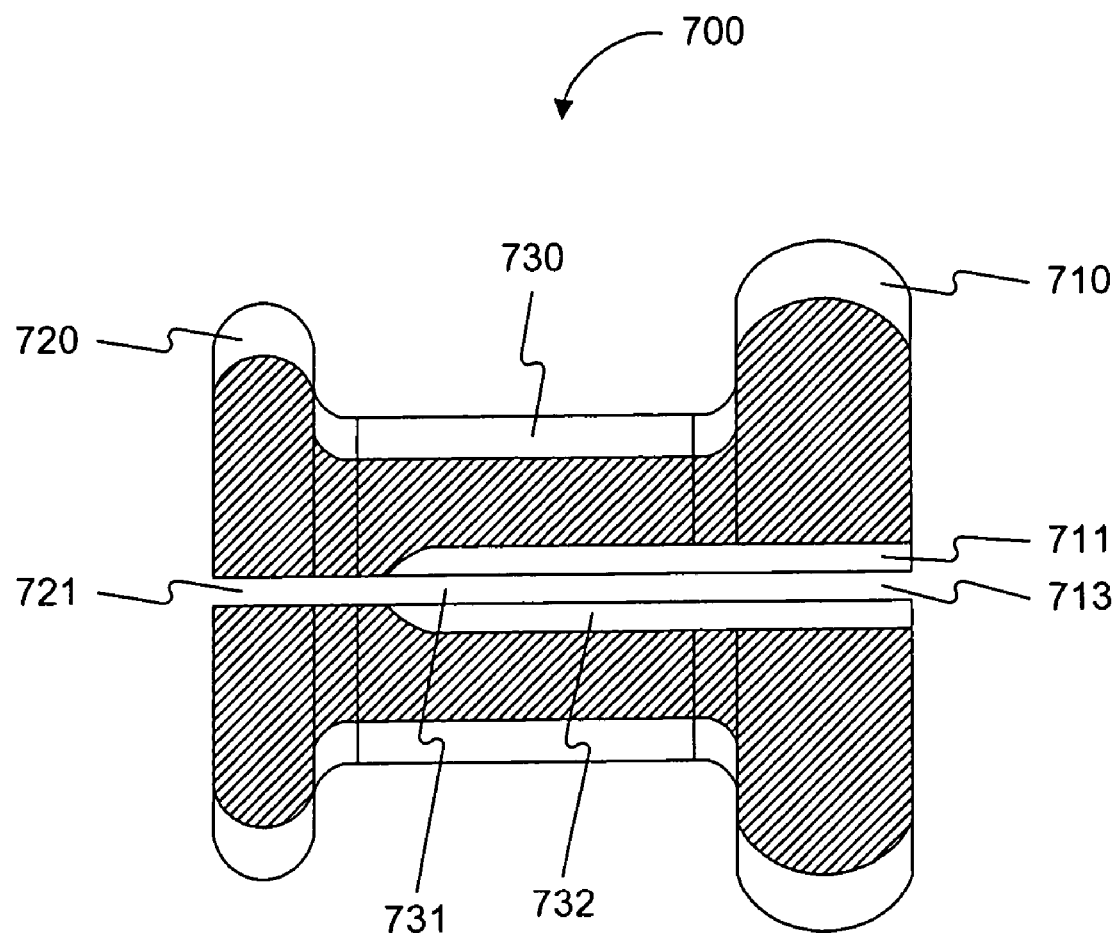
FIG. 8B is a cross-sectional view of the handle portion of FIG. 8A.
Figure 8C:
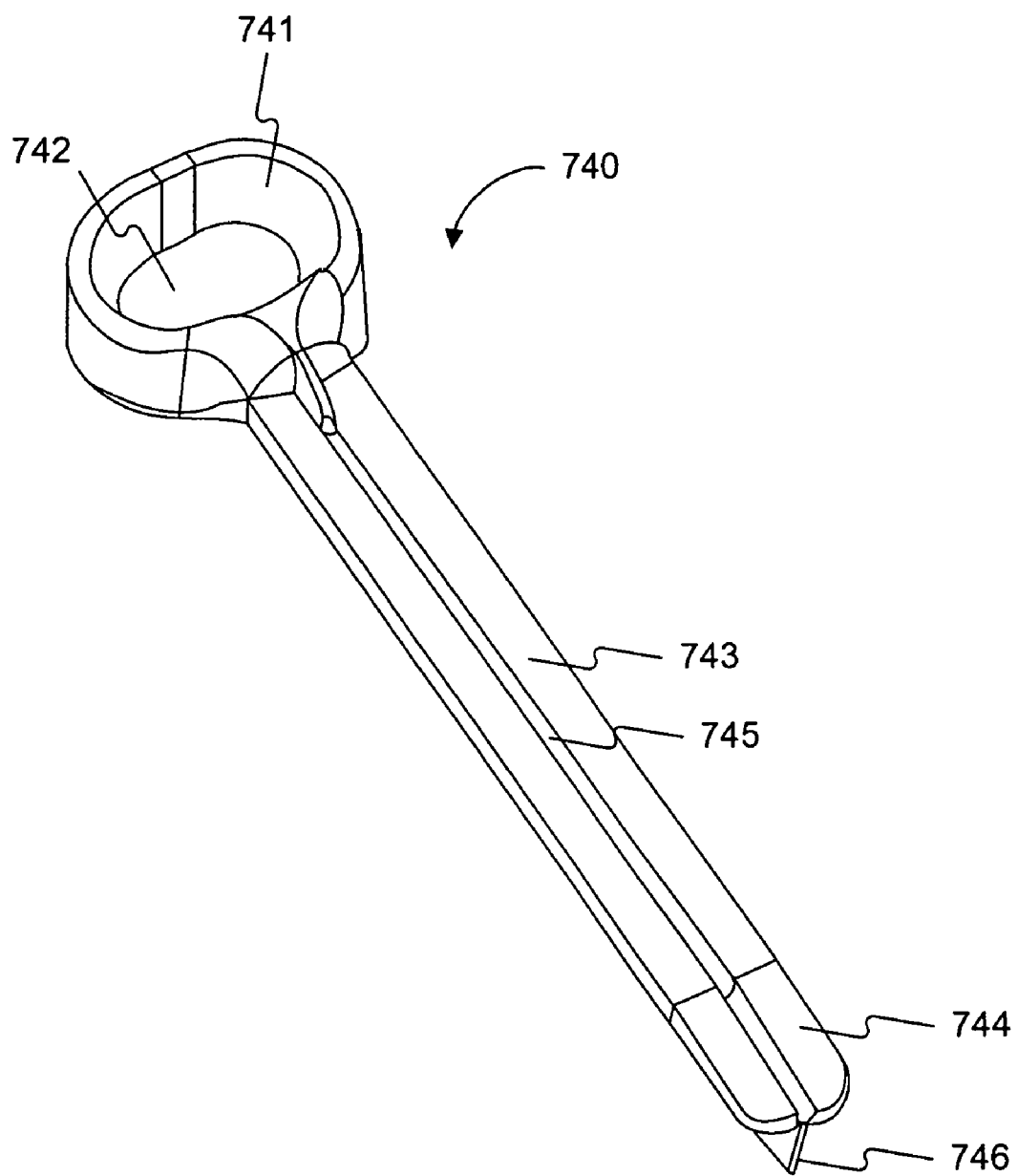
FIG. 8C is a perspective view of an elongate portion for use with the handle portion of FIG. 8A.

Yet another embodiment of a spool-like device is depicted in FIGS. 8A-8C. The device 700 has a proximal portion 710, a distal portion 720, and a central portion 730. The proximal portion 710 has a radial groove 711, a grooved throughhole 712, and a narrower groove 713. The narrower groove 713 connects the radial groove 711 to the grooved throughhole 712. The radial groove 711 has a width sufficient to receive a member 14 and an assembly 15. The narrower groove 713 extends through central portion 730 via narrower groove 731 and terminates at groove 721 in the distal portion 720. The radial groove 711 continues through at least a portion of the central portion 730 via wider groove 732. Wider groove 732 also has a width sufficient to receive a member 14 and an assembly 15, and tapers at its distal end so that it is configured, for example, to receive the end of the assembly 15. The depth of the wider groove 732 is sufficient to retain member 14, for example, at least about one-half the diameter of the member 14, so as to allow the member 14 and assembly 15 to be press-fit into the wider groove 732. In coiling and/or storing the member 14 and assembly 15 in this embodiment, loops of the member 14 may be placed in the radial groove 711. The last portion of the member 14, which is connected to the assembly 15, may then be placed in the grooves 711, 732 with the assembly 15 being placed at the distal end of the wider groove 732, and the member 14 extending out proximally from the groove 711.

The grooved throughhole 712 is configured to receive an elongate portion of the handle 10, for example, as shown in FIG. 8C. The elongate portion 740 has a thumb ring 741 defining a thumb hole 742 therein, and an elongate T-shaped portion 743 with a groove 745 extending until it becomes a tapered T-shaped portion 744. The tapered T-shaped portion 744 is configured to be placed in the grooved throughhole 712 such that the ridge 714 is placed in the groove 745, and the vertical portion 746 is at least partially placed in the narrower groove 713. The T-shaped portion 744 may serve several purposes, for example, it may be used to align the elongate portion 740 in the device 700 and/or it may impart strength to the elongate portion 740 (i.e., make the elongate portion 740 more resistant to strains and/or torsional stresses). In various embodiments, however, the T-shaped portion need not be T-shaped, and may instead have any desired cross-sectional geometry.

In the various embodiments, the location of the grooves and/or notches on the device relative to each other may changed as desirable. For example, the grooves and/or notches may be on opposite sides of the proximal and/or distal portions. Additionally, the grooves and/or notches may be sized to accommodate a member 14 having any number of diameters and/or any number of lengths. For example, the grooves and/or notches may be configured (i.e., have widths and lengths and numbers) to accommodate any number of loops of the member 14 having any diameter. Furthermore, any of the features depicted in the embodiments shown in FIGS. 1-8C may be removed and/or they may be mixed and/or combined with any other features in those other embodiments. For example, in the various embodiments, any of the proximal portions may be substituted for any of the distal portions and vice versa. Along those lines, it should be understood that the use of the terms proximal and distal are exemplary only, and are not meant to limit any of the embodiments to any particular orientation and/or configuration. In addition, all the loops of the member 14 (including the one with the assembly 15) may be placed inside one sufficiently sized groove on the device. Additionally, the grooves and/or notches may be composed of at least one material configured to allow the grooves and/or notches to more effectively grip and/or retain at least a portion of the end effector assembly 15. The at least one material may comprise all or any portion of the spool, proximal portion, distal portion, grooves, and/or notches.

The principles and features of the invention set forth herein, for example when used in conjunction with endoscopic instruments, provide several advantages over conventional devices. For example, by storing the assembly 15 on a portion of the instrument, such as the spool-like device of the handle, the need for a distal cap on the assembly 15 is eliminated, reducing the number of parts and amount of material necessary. Eliminating the distal cap also eliminates possibilities that the cap, left unremoved from the instrument, may become lodged in the endoscope. Material is also saved as the volume of the handle is reduced, for example, by placing notches, grooves, and channels in the spool-like portion of the handle. In another example, the tendency of the catheter to become twisted and tangled, as it is prone to do in the conventional arrangement, is reduced, making the instrument less cumbersome and time consuming to unpack and prepare for use. In yet another example, embodiments of the invention allow the user to recoil the member 14 of the device after use, allowing for safer disposal of the device.

In various embodiments, the various features of the invention set forth above may be used in any medical or non-medical procedure with any medical or non-medical device. For example, the principles of the invention may be used in connection with other types of medical device handles, such as scissors-like handles or any other suitable handles.

In embodiments that use an endoscopic instrument having an elongate member and an end effector assembly, which may include an end effector assembly accommodation device, in an endoscopic medical procedure, the elongate endoscopic instrument can be advanced down the working channel of an endoscope, through the working channel cap that has a seal specifically designed for use with the elongate endoscopic instrument, and into a tissue tract. When adjacent to the tissue sites, the end effector assembly of the elongate endoscopic instrument can be actuated, for example, taking and storing one or multiple biopsy samples using a biopsy forceps device, and then be extracted from the tissue tract through the working channel of the endoscope.

Other embodiments of the invention will be apparent to those skilled in the art from consideration of the specification and practice of the invention disclosed herein. The specification and examples are exemplary only, with a true scope and spirit of the invention being indicated by the following claims.

What is claimed is:

1. A medical device comprising:
   a handle;
   an end effector assembly; and
   an elongate, flexible member connecting the handle to the end effector assembly,
   wherein the handle includes an elongate portion and a spool portion disposed around the elongate portion, wherein the spool portion includes a proximal portion and a distal portion connected by a central portion, wherein a plurality of grooves are defined by the proximal portion and another plurality of grooves are defined by the distal portion, and at least one groove accommodates a portion of the end effector assembly, the spool portion being configured to actuate the end effector assembly, and
   wherein at least one of the plurality of grooves and at least one of the another plurality of grooves are circumferentially aligned with each other and are discontinuous with the central portion.

2. The medical device of claim 1, wherein the at least one groove is configured to receive at least one half of a diameter of the elongate member.

3. The medical device of claim 1, wherein a width of the at least one groove is substantially the same as a diameter of the elongate member.

4. The medical device of claim 1, wherein the at least one groove is defined by the proximal portion.

5. The medical device of claim 1, wherein the at least one groove is defined by the distal portion.

6. The medical device of claim 1, wherein the at least one groove extends through the proximal portion, the central portion, and the distal portion.

7. The medical device of claim 6, wherein a portion of the at least one groove is wider than the rest of the at least one groove.

8. The medical device of claim 1, wherein the at least one groove is configured to accommodate more than one portion of the elongate member.

9. The medical device of claim 1, wherein the at least one groove comprises at least two grooves.

10. The medical device of claim 9, wherein one of the at least two grooves is configured to accommodate more than one portion of the elongate member and the other of the at least two grooves is configured to accommodate one portion of the elongate member.

11. The medical device of claim 1, wherein the handle further comprises a channel.

12. The medical device of claim 11, wherein the channel is defined by the spool portion of the handle.

13. The medical device of claim 12, wherein the channel is defined by the distal portion.

14. The medical device of claim 13, wherein the at least one groove is defined by the proximal portion, and
   wherein a circumferential position of the at least one groove on the proximal portion is aligned with a circumferential position of the channel on the distal portion.

15. The medical device of claim 1, wherein the at least one groove is defined by the proximal portion and the central portion.

16. The medical device of claim 1, wherein the handle further comprises a notch.

17. The medical device of claim 16, wherein the notch is defined by the spool portion of the handle.

18. The medical device of claim 17, wherein the notch is defined by the distal portion.

19. The medical device of claim 18, wherein the at least one groove is on the proximal portion, and
   wherein the at least one groove and the notch are on corresponding portions of the proximal portion and the distal portion, respectively.

20. The medical device of claim 1, wherein the at least one groove is configured to receive a loop of the elongate member.

21. The medical device of claim 1, wherein the at least one groove is configured to receive loops of the elongate member.

22. The medical device of claim 1, wherein the at least one groove includes a radial groove and a circumferential groove.

23. The medical device of claim 22, wherein the radial groove and circumferential groove are connected.

24. The medical device of claim 1, further comprising a throughhole on the spool portion configured to accommodate the elongate portion therethrough.

25. The medical device of claim 1, further comprising a throughhole extending through the proximal portion, central portion, and distal portion.

26. The medical device of claim 1, wherein the end effector assembly is a pair of opposing biopsy forceps jaws.

27. The medical device of claim 1, wherein the at least one groove is defined by the central portion.

28. The medical device of claim 1, wherein the portion of the handle that defines the at least one groove is composed of a material configured to assist in retaining the portion of the end effector assembly.

29. The medical device of claim 16, wherein the portion of the handle that comprises the notch is composed of a material configured to assist in retaining the end effector of the end effector assembly.

30. The medical device of claim 1, wherein each of the plurality of grooves is separated from each other along an outer circumference of the proximal portion, and each of the another plurality of grooves is separated from each other along an outer circumference of the distal portion, wherein at least one of the plurality of grooves and the another plurality of grooves houses multiple loops of the elongate member.

31. The medical device of claim 1, wherein the plurality of grooves are circumferentially aligned with the another plurality of grooves.

32. The medical device of claim 1, wherein one groove of the plurality of grooves and the another plurality of grooves accommodates multiple loops of the elongate member.

33. A medical device comprising:
a handle;
an end effector assembly; and
an elongate, flexible member connecting the handle to the end effector assembly,
wherein the handle includes an elongate portion and a spool portion disposed around the elongate portion, wherein the spool portion includes a proximal portion and a distal portion connected by a central portion, wherein a plurality of grooves are defined by the proximal portion and another plurality of grooves are defined by the distal portion, wherein the plurality of grooves are circumferentially aligned with the another plurality of grooves, and a plurality of loops of the elongate member is disposed in a groove defined by the handle, the spool portion being configured to actuate the end effector assembly, and
wherein at least one of the plurality of grooves and at least one of the another plurality of grooves are circumferentially aligned with each other and are discontinuous with the central portion.

34. The medical device of claim 33, wherein a plurality of portions of the elongate member are disposed in the plurality of grooves.

35. The medical device of claim 33, further comprising a channel.

36. The medical device of claim 33, further comprising a notch.

37. The medical device of claim 33, wherein a plurality of portions of the elongate member are disposed in the groove.

38. The medical device of claim 33, further comprising a channel defined by the spool portion.

39. The medical device of claim 33, wherein the groove is defined by the proximal portion.

40. The medical device of claim 33, wherein the groove is defined by the distal portion.

41. The medical device of claim 33, wherein one portion of the elongate, flexible member is disposed in one of the plurality of grooves and another portion of the elongate, flexible member is disposed in one of the another plurality of grooves.

42. The medical device of claim 33, wherein a portion of the end effector assembly is disposed in another groove defined by the proximal portion and the central portion.

43. The medical device of claim 33, wherein at least some of the plurality of loops are disposed in separate grooves.

44. The medical device of claim 33, wherein at least some of the plurality loops are disposed in separate pairs of grooves.

45. The medical device of claim 33, further comprising a channel defined by the handle.

46. The medical device of claim 33, further comprising a notch defined by the handle.

47. The medical device of claim 33, wherein the end effector assembly is a pair of opposing biopsy forceps jaws.

48. The medical device of claim 33, wherein a portion of the end effector assembly is disposed in the groove defined by the handle.

49. The medical device of claim 33, wherein each of the plurality of grooves is separated from each other along an outer circumference of the proximal portion, and each of the another plurality of grooves is separated from each other along an outer circumference of the distal portion, wherein at least one of the plurality of grooves and the another plurality of grooves houses the plurality of loops of the elongate member.

50. A medical device comprising:
a handle including an elongate portion and a spool portion including a proximal portion, a central portion, and a distal portion and disposed around the elongate portion;
an end effector assembly, wherein the spool portion is configured to actuate the end effector assembly; and
an elongate, flexible member connecting the handle to the end effector assembly,
wherein the handle defines a groove, wherein the groove accommodates a plurality of loops of the elongate member and a portion of the end effector assembly,
wherein the spool defines at least one notch circumferentially adjacent to the groove on the proximal portion of the spool and at least another notch circumferentially adjacent to the groove on the distal portion of the groove, one or more of the at least one notch and the at least another notch being configured to accommodate a portion of the elongate member, and
wherein the at least one notch and the at least another notch are circumferentially aligned with each other and are discontinuous with the central portion.

51. The medical device of claim 50, wherein the groove is defined by the spool portion.

52. The medical device of claim 50, wherein the portion of the elongate member is disposed in one or more of the at least one notch and the at least another notch.

53. The medical device of claim 50, wherein each of the at least one notch and the at least another notch has a width substantially the same as a diameter of the elongate member.

54. The medical device of claim 50, wherein each of the at least one notch and the at least another notch has a width narrower than a diameter of the elongate member.

55. A medical device comprising:
a handle;
an end effector assembly; and
an elongate, flexible member forming a plurality of loops and connecting the handle to the end effector assembly;
wherein the handle includes a spool portion, the spool portion including a proximal portion and a distal portion connected by a central portion, wherein a first plurality of grooves are arranged along an outer circumference of the proximal portion and a second plurality of grooves are arranged along an outer circumference of the distal portion, wherein the first plurality of grooves are circumferentially aligned with the second plurality of grooves, wherein each of the grooves of the first plurality of grooves is separated from each other along the outer circumference of the proximal portion, and each of the grooves of the second plurality of grooves is separated from each other along the outer circumference of the distal portion, and one of the first and second plurality of grooves houses the plurality of loops, the spool portion being configured to actuate the end effector assembly, and
wherein at least one of the first plurality of grooves and at least one of the second plurality of grooves are circumferentially aligned with each other and are discontinuous with the central portion.

56. The medical device of claim 54, wherein the one of the first and second plurality of grooves houses the end effector assembly.

* * * * *